(12) United States Patent
Schroer, Jr. et al.

(10) Patent No.: US 7,435,244 B2
(45) Date of Patent: Oct. 14, 2008

(54) DIAPER DESIGN HAVING ZONES OF REDUCED STIFFNESS AND CONTINUOUS BREATHABILITY

(75) Inventors: Charles Frederick Schroer, Jr., Camden, AR (US); Glenn Ernest Glasscock, Camden, AR (US); Charles Augustus Hart, Little Rock, AR (US); John L. Moody, Camden, AR (US); Meredith Gaye Tharp, Camden, AR (US); Jason Brian Woodard, Camden, AR (US)

(73) Assignee: Arquest, Inc., Cranbury, NJ (US)

( * ) Notice: Subject to any disclaimer, the term of this patent is extended or adjusted under 35 U.S.C. 154(b) by 841 days.

(21) Appl. No.: 10/612,601

(22) Filed: Jul. 1, 2003

(65) Prior Publication Data

US 2005/0004543 A1    Jan. 6, 2005

(51) Int. Cl.
A61F 13/494    (2006.01)
(52) U.S. Cl. .................. 604/385.27; 604/385.28; 604/378
(58) Field of Classification Search . 604/285.24–285.3, 604/385.01, 385.101, 378
See application file for complete search history.

(56) References Cited

U.S. PATENT DOCUMENTS

| | | | |
|---|---|---|---|
| 4,050,462 A | 9/1977 | Woon et al. | |
| 4,573,986 A | 3/1986 | Minetola et al. | 604/366 |
| 4,636,207 A | 1/1987 | Buell | 604/370 |
| 4,662,875 A | 5/1987 | Hirotsu et al. | 604/389 |
| 4,681,578 A | 7/1987 | Anderson et al. | |
| 4,695,278 A | 9/1987 | Lawson | 604/385 |
| 4,701,170 A | 10/1987 | Wilson et al. | |
| 4,704,116 A | 11/1987 | Enloe | |
| 4,710,187 A | 12/1987 | Boland et al. | |
| 4,738,677 A * | 4/1988 | Foreman | 604/385.27 |
| 4,743,246 A * | 5/1988 | Lawson | 604/385.27 |
| 4,795,454 A | 1/1989 | Dragoo | |
| 4,798,603 A | 1/1989 | Meyer et al. | 604/378 |
| 4,808,178 A | 2/1989 | Aziz et al. | |
| 4,846,815 A | 7/1989 | Scripps | 604/391 |
| 4,846,825 A | 7/1989 | Enloe et al. | |
| 4,883,480 A | 11/1989 | Huffman et al. | |
| 4,900,317 A | 2/1990 | Buell | 604/370 |
| 4,904,251 A * | 2/1990 | Igaue et al. | 604/385.26 |
| 4,909,803 A | 3/1990 | Aziz et al. | |

(Continued)

FOREIGN PATENT DOCUMENTS

EP    1106151 A2 *  6/2001

(Continued)

Primary Examiner—Karin M Reichle
(74) Attorney, Agent, or Firm—Dickstein Shapiro LLP

(57) ABSTRACT

An absorbent article, such as a disposable diaper, having a topsheet, barrier cuffs, an optional acquisition layer, an absorbent core, a barrier layer, and a backsheet. The diaper is arranged so as to create breathable zones of reduced stiffness surrounding the wearer's thighs. That is, the layers of material forming the diaper are arranged so the area surrounding the wearer's thighs includes only the backsheet, barrier cuffs and leg elastics. No liquid-impervious material is present within the breathable zones of reduced stiffness. Furthermore, these breathable zones of reduced stiffness preferably are formed so that only hydrophobic material is present. Thus, providing a better fitting, less irritating absorbent article by reducing the stiffness and increasing the breathability of the diaper in the area surrounding the wearer's thighs, resulting in increased comfort and fit around the wearer's thighs.

48 Claims, 5 Drawing Sheets

U.S. PATENT DOCUMENTS

| | | | |
|---|---|---|---|
| 4,938,753 A | 7/1990 | Van Gompel et al. | |
| 4,938,754 A | 7/1990 | Mesek | |
| 4,938,757 A | 7/1990 | Van Gompel et al. | 604/396 |
| 4,940,464 A | 7/1990 | Van Gompel et al. | 604/396 |
| 4,963,140 A | 10/1990 | Robertson et al. | 604/389 |
| 5,019,065 A | 5/1991 | Scripps | |
| 5,085,654 A | 2/1992 | Buell | 604/370 |
| 5,156,793 A | 10/1992 | Buell et al. | 264/288 |
| 5,167,897 A | 12/1992 | Weber et al. | 264/288 |
| 5,263,948 A | 11/1993 | Karami et al. | 604/383 |
| 5,286,543 A | 2/1994 | Ungpiyakul et al. | 428/74 |
| 5,292,316 A | 3/1994 | Suzuki | |
| 5,318,555 A | 6/1994 | Siebers et al. | 604/390 |
| 5,364,382 A | 11/1994 | Latimer et al. | 604/378 |
| RE34,920 E | 4/1995 | Aziz et al. | |
| 5,415,644 A | 5/1995 | Enloe | |
| 5,429,629 A | 7/1995 | Latimer et al. | 604/378 |
| 5,476,458 A * | 12/1995 | Glaug et al. | 604/378 |
| 5,496,298 A | 3/1996 | Kuepper et al. | 604/389 |
| 5,509,915 A | 4/1996 | Hanson et al. | 604/378 |
| 5,562,650 A | 10/1996 | Everett et al. | 604/378 |
| 5,599,338 A | 2/1997 | Enloe | |
| 5,624,424 A * | 4/1997 | Saisaka et al. | 604/385.28 |
| 5,643,239 A | 7/1997 | Bodford et al. | 604/370 |
| 5,643,243 A | 7/1997 | Klemp | |
| 5,643,588 A | 7/1997 | Roe et al. | 424/402 |
| 5,674,215 A * | 10/1997 | Ronnberg | 604/385.28 |
| 5,674,216 A | 10/1997 | Buell et al. | |
| 5,827,259 A | 10/1998 | Laux et al. | |
| 5,843,056 A | 12/1998 | Good et al. | 604/367 |
| 5,843,066 A | 12/1998 | Dobrin | |
| 5,879,341 A | 3/1999 | Odorzynski et al. | 604/367 |
| 5,928,209 A | 7/1999 | Bodford et al. | 607/370 |
| 5,947,946 A | 9/1999 | Fisher et al. | |
| 5,968,025 A | 10/1999 | Roe et al. | 604/364 |
| 5,993,433 A | 11/1999 | St. Louis et al. | |
| 6,068,620 A | 5/2000 | Chmielewski | 604/378 |
| 6,102,892 A | 8/2000 | Putzer et al. | |
| 6,107,537 A | 8/2000 | Elder et al. | 604/364 |
| 6,118,041 A | 9/2000 | Roe et al. | 604/360 |
| 6,153,209 A | 11/2000 | Vega et al. | 424/404 |
| D437,933 S | 2/2001 | Fletcher et al. | D24/126 |
| 6,297,424 B1 | 10/2001 | Olson et al. | 604/361 |
| 6,494,872 B1 | 12/2002 | Suzuki et al. | |
| 6,648,867 B2 * | 11/2003 | Minato et al. | 604/385.04 |
| 2001/0003153 A1 * | 6/2001 | Sayama et al. | 604/385.28 |

FOREIGN PATENT DOCUMENTS

JP  2001-149409 A  *  6/2001

* cited by examiner

DIAPER DESIGN HAVING ZONES OF REDUCED STIFFNESS AND CONTINUOUS BREATHABILITY

BACKGROUND OF THE INVENTION

Absorbent articles, such as infant diapers, are well known in the art. These articles are inexpensive, often disposable, and capable of absorbing and retaining fluids and other bodily discharges. Examples of prior art diapers are shown in FIGS. 1, 2, and 2a. These absorbent articles typically contain a liquid-pervious topsheet 1 manufactured from a hydrophilic material, a liquid-impervious backsheet 2 manufactured from a hydrophobic material, and an absorbent structure disposed between the topsheet 1 and backsheet 2. The absorbent structure consists of an absorbent core 3 disposed between an impervious film layer 8 and an acquisition layer 7. Prior art diapers may further include leg elastic gathers 4, leg openings 5, and elasticated barrier cuffs 6.

A serious problem associated with absorbent articles is "lateral leakage," the leakage of body exudates out of the gaps between the absorbing article and the wearer's legs because body exudates are not immediately absorbed by the core and travel laterally across the inner surface of the diaper. One solution that has been developed to prevent lateral leakage is to elasticate the leg openings using leg elastic gathers 4 so that the absorbent article fits more securely to the wearer's thighs, thereby reducing gaps.

Another solution that has been developed is to provide elasticated barrier cuffs 6 adjacent to the absorbent core 3 and inboard of the leg elastic gathers 4 to further inhibit movement of fluids and exudates toward the leg openings 5.

There is however, a limitation to how well elasticated leg openings can fit around a wearer's thighs. This limitation is dictated by, among other things, the stiffness of the required liquid-impervious layer. Such stiff, nonwoven and plastic film laminates used to form the liquid-impervious backsheet causes resistance to the elastic strands, which limits the degree of gather formation at the leg openings, typically resulting in large gathers that leave gaps for potential leakage. Furthermore, a stiff nonwoven and plastic film laminate results in the leg opening regions becoming stiff, in turn leading to problems with fit generally and sealing in particular, as stiff, bunched material does not conform to a wearer's thighs, thus leaving gaps and increasing lateral leakage. In addition, stiffer laminates require a stronger elastic force to provide the required leg elastication, which in turn results in a stiffer seal around the wearer's thighs leading to unwanted irritation.

In addition, the use of liquid-impervious material in an absorbent article, especially in the leg opening regions of a diaper, results in decreased breathability, which in turn leads to rashes and further irritation. This is because liquid-impervious material does not permit moisture to escape, thus trapping the moisture against the wearer's thighs, resulting in rashes and irritation. It is known to form the backsheet from breathable materials, that is, materials which permit vapors to escape from the absorbent core 3 while preventing liquids and exudates from passing through. However, even when using so-called "vapor permeable" liquid barrier layers, the free escape of moist air from inside the diaper is significantly impeded by the presence of the barrier layer.

Manufacturers have made numerous attempts to construct absorbent articles capable of preventing or reducing lateral leakage. For example, U.S. Pat. No. 5,947,946 to Fisher et al. discloses a diaper consisting of a liquid-pervious topsheet 24, a liquid-impervious backsheet 26, an absorbent core 28 and elasticized leg gathers 32 to prevent lateral discharge of exudates. The length and width dimensions of the liquid-pervious topsheet and liquid-impervious backsheet are larger than the absorbent core and extend to form the outer perimeter of the diaper. The elasticized leg gathers are located laterally outboard of the absorbent core and are in between the liquid-pervious topsheet and liquid-impervious backsheet. A disadvantage with this design is the plastic backsheet which extends into the leg opening regions and results in deceased breathability in those regions and impaired fit around the leg due to the stiffness imparted by the additional layer of plastic backsheet.

Manufacturers have also made attempts to increase comfort by increasing the breathability of disposable diapers. Such attempts included the design of diapers using "zone laminates," the use of liquid-impervious material for only a portion of the diaper's width, thus enabling diapers to be more comfortable while still being liquid-impervious in the crotch region to prevent the escape of body exudates.

For example, U.S. Pat. No. 5,263,948 to Karami et al. discloses a diaper consisting of a liquid-pervious topsheet 40, a liquid-pervious backsheet 12, an absorbent core 38, a liquid-impervious dam 28 and elasticized leg gathers 42 to prevent lateral discharge of exudates. The length and width dimensions of the liquid-pervious topsheet and backsheet are larger than the length and width dimensions of the absorbent core and liquid-impervious dam. Elasticized leg gathers are further provided between the liquid-pervious topsheet and backsheet, and located laterally outboard of the absorbent core and dam. Thus, an area surrounding the wearer's thighs consisting only of liquid-pervious material is created. A disadvantage with this design is that the liquid-impervious dam extends to, and wraps around, the side edges of the absorbent core in order to prevent body exudates from escaping through the back of the diaper or leaking through the side edges of the core. Wrapping the impervious dam around the absorbent core results in body exudates landing on the portion of the impervious material which overlays the absorbent core, causing body exudates to flow to the diaper's backsheet. A further disadvantage with this design is that the liquid-pervious topsheet is manufactured from a hydrophilic material, while the liquid-pervious backsheet is manufactured from a hydrophobic material. Thus, the region surrounding the wearer's leg consists of a combination of hydrophilic and hydrophobic material, which results in potential wetness around the wearer's legs due to the hydrophilic material wicking moisture out to its lateral edges.

An immense amount of research has been devoted to the design of absorbent articles—for example, an electronic database search for patents directed to diaper backsheet cuffs or flaps designs, run on the United States Patent and Trademark Office website, yields many hundreds of results. Despite this research, there still remains a need for a more comfortably fitting absorbent article capable of containing urinary and fecal excretions while minimizing irritation to the wearer. The present invention addresses the problems of lateral leakage and wearer irritation discussed above by providing an absorbent article with zones of: (i) reduced stiffness and (ii) continuous breathability, in the area surrounding the wearer's legs. These breathable zones of reduced stiffness improve leg gather formation and reduce irritation to the wearer's skin, resulting in a better fitting absorbent article, with reduced lateral leakage. These zones also permit the absorbent article to provide additional breathability around the leg openings, which helps prevent unwanted rashes and additional irritation.

SUMMARY OF THE INVENTION

The present invention relates to an absorbent article, such as a disposable diaper, that improves leg gather formation in the leg opening regions, thus providing a better fitting, less irritating absorbent article capable of preventing lateral leakage. This is accomplished by reducing the amount of liquid-impervious material used in the manufacture of the absorbent article, such that only liquid-pervious material, preferably hydrophobic liquid-pervious material, exists in the leg opening regions and diaper ears.

Generally speaking, the present inventions relates to an absorbent article having (from the skin-facing side outwardly), a topsheet, barrier cuffs, an optional acquisition layer, an absorbent core, a barrier layer, and a backsheet. The absorbent articles being arranged so as to create zones of reduced stiffness and continuous breathability ("breathable zones of reduced stiffness") surrounding the wearer's legs. That is, the layers of material forming the absorbent article are arranged so the area surrounding the wearer's thighs includes only the backsheet, barrier cuffs, and leg elastics. No liquid-impervious material is present within the breathable zones of reduced stiffness, thus helping to prevent unwanted irritation.

In addition, preferably these breathable zones of reduced stiffness are formed so that only hydrophobic material is present, thus further reducing the possibility of moisture wicking to the leg regions, resulting in increased comfort and fit around the wearer's thighs.

One embodiment of the present invention is directed to an absorbent article comprising a liquid-pervious backsheet and topsheet, a pair of liquid-pervious barrier cuffs bonded to the topsheet, an absorbent core disposed between the topsheet and the backsheet, a liquid-impervious barrier layer disposed between the absorbent core and the backsheet, and leg elastic members. The invention being defined by the barrier layer not being present in the portion of the article where the leg elastic members are located, and the barrier layer does not wrap around the absorbent core.

The present invention further relates to an absorbent article wherein preferably the topsheet and/or absorbent core are also not present in the portion of the article where the leg elastic members are located. That is, preferably the barrier layer, the absorbent core, and/or topsheet have lateral edges which are located laterally inboard of the leg elastics thus creating breathable zones of reduced stiffness.

Another embodiment of the present invention is directed to an absorbent article comprising a liquid-pervious hydrophobic backsheet, a liquid-pervious hydrophilic topsheet, a pair of liquid-pervious hydrophobic barrier cuffs bonded to the topsheet, an absorbent core disposed between the topsheet and the backsheet, a liquid-impervious barrier layer disposed between the absorbent core and the backsheet, and leg elastic members. The inventions being defined by the barrier layer not being present in the portion of the article where the leg elastic members are located.

The present invention further relates to an absorbent article wherein preferably the topsheet and/or absorbent core are also not present in the portion of the article where the leg elastic members are located. That is, preferably the barrier layer, the absorbent core, and/or topsheet have lateral edges which are located laterally inboard of the leg elastics thus creating breathable zones of reduced stiffness.

Another embodiment of the present invention is directed to an absorbent article comprising a liquid-pervious hydrophobic backsheet, a liquid-pervious hydrophilic topsheet, a pair of liquid-pervious hydrophobic barrier cuffs bonded to the topsheet, an absorbent core disposed between the topsheet and the backsheet, a liquid-impervious barrier layer disposed between the absorbent core and the backsheet, and breathable zones of reduced stiffness located in the portions of the article beyond the edges of the barrier layer.

The present invention further relates preferably to an absorbent article wherein the breathable zones of reduced stiffness comprise portions of the absorbent article which do not encompass any liquid-impervious material. More preferably, the breath zones of reduced stiffness comprise portions of the absorbent article which do not encompass any hydrophilic material.

DEFINITIONS

Figure 1:
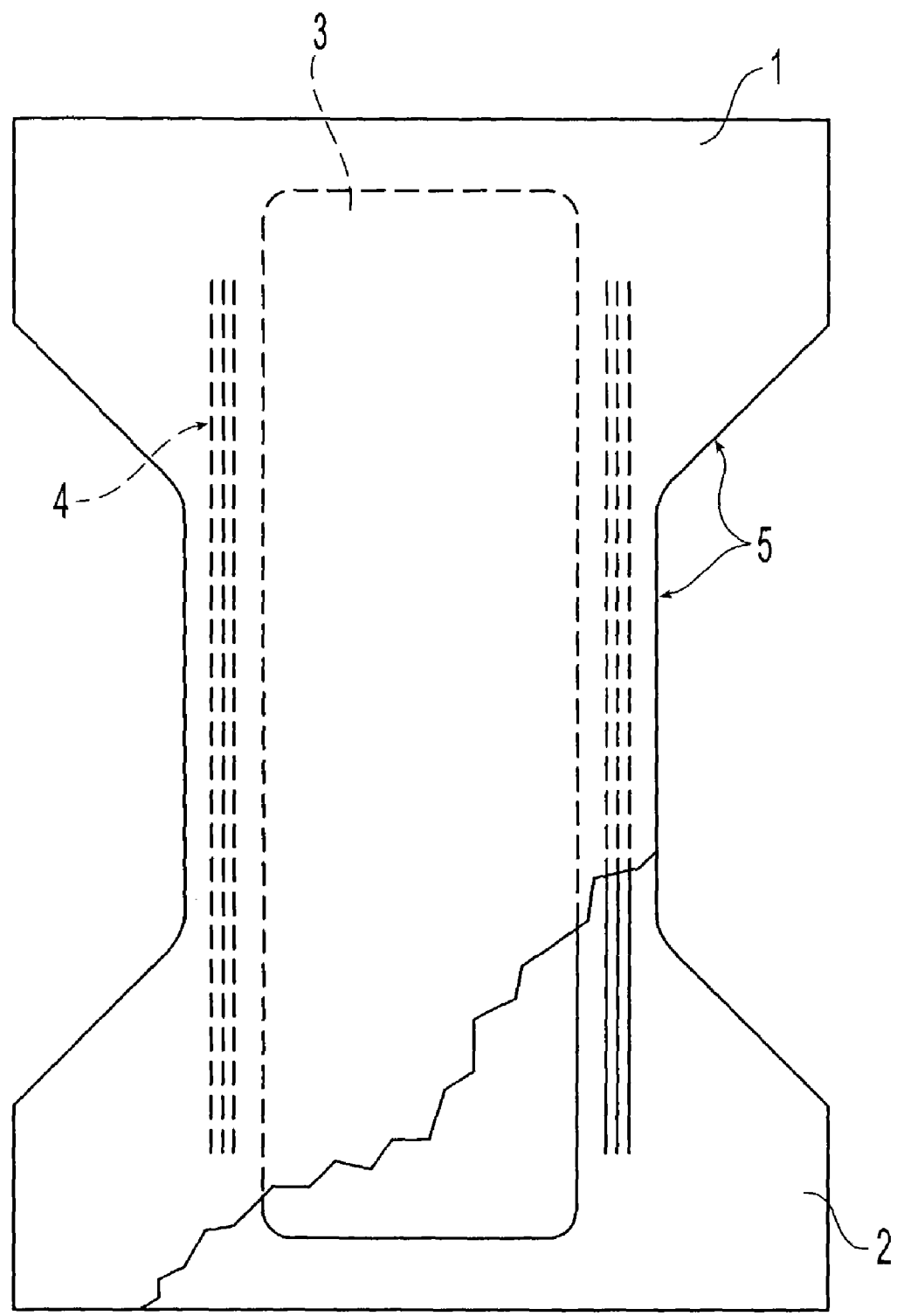
FIG. 1 is a perspective view of a diaper embodiment known in the prior art.
Figure 2:
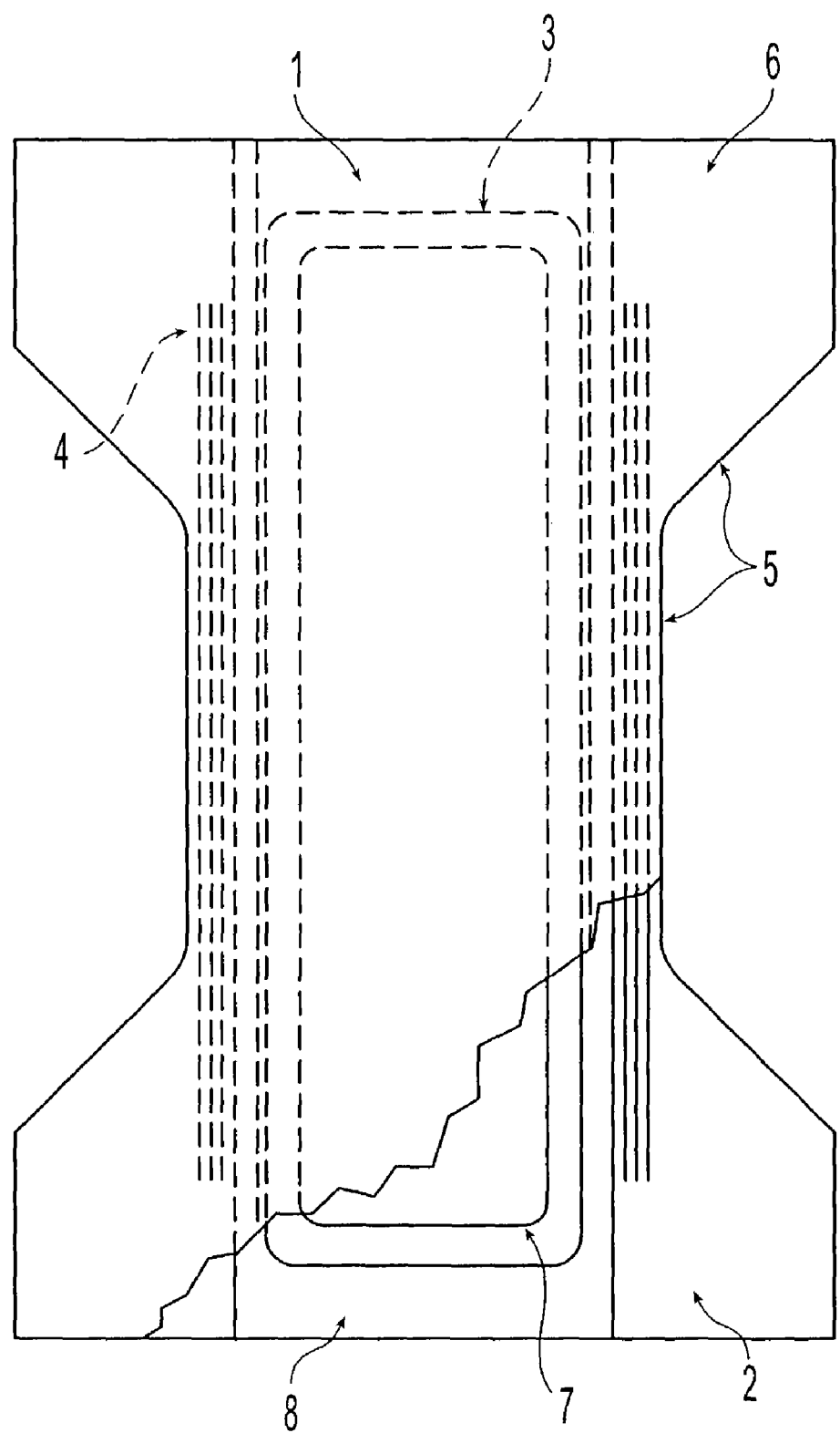
FIG. 2 is a perspective view of an alternate diaper embodiment known in the prior art.
Figure 2A:
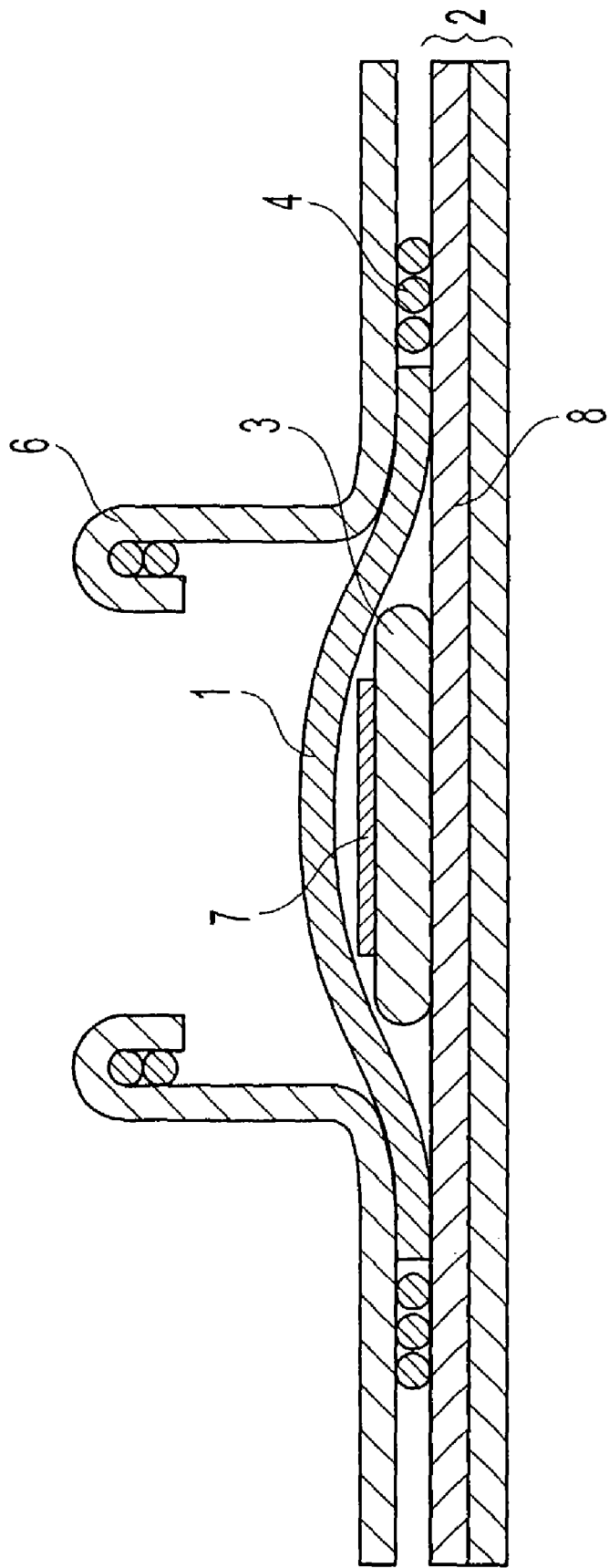
FIG. 2a is a cross sectional view of the absorbent article in FIG. 2.

Each of the following terms used herein include the following meaning:

"Absorbent article" refers to an article capable of absorbing and containing exudates. More specifically, it refers to articles which are placed against or in proximity to the body of the wearer to absorb and contain the various exudates discharged from the body. A non-exhaustive list of examples include diapers, diaper covers, disposable diapers, training pants, feminine hygiene products and adult incontinence products. The claims of the present invention are intended to cover all of the foregoing classes of absorbent articles, without limitation.

"Pervious," means that the material will allow fluid to pass through. Accordingly, it refers to all non-woven material given the fact that they will allow fluid to pass through them at pressures encountered under standard use.

"Impervious" means that the material will not allow fluid to pass through. Accordingly, as used herein, it refers to the use of a plastic film alone, or in a laminate with non-woven material, to further block fluid flow under standard use conditions.

Use of the modifier "hydrophobic" when describing a material indicates that the material will repel fluid, under standard use conditions.

Use of the modifier "hydrophilic" when describing a material indicates that the material will accept fluid, under standard use conditions.

DESCRIPTION OF THE PREFERRED EMBODIMENTS

In accordance with an embodiment of the present invention, a standard disposable diaper as is well known in the art is disclosed, such as in U.S. Pat. Nos. 5,947,946; 6,102,892, and 6,068,620. Again, it should be noted however, that the present invention is applicable to other types of absorbent articles, but for simplicity the invention will be described as used with a diaper.

For the purpose of promoting an understanding of the principles of the present invention, reference will now be made to an exemplary, non-limiting embodiment illustrated in FIGS. 3 and 4. As shown, preferably the diaper 10 is of laminate construction comprising (from the skin-facing side outwardly), a topsheet 20, barrier cuffs 21a, 21b, an optional acquisition layer 60, an absorbent core 30, a barrier layer 40, and a backsheet 50.

The diaper 10 is arranged so as to create zones of reduced stiffness and continuous breathability 70 ("breathable zones of reduced stiffness") surrounding the wearer's legs. That is, the layers of material forming the diaper 10 are arranged so the area surrounding the wearer's thighs includes only the backsheet 50, barrier cuffs 21a, 21b and leg elastics 125. No liquid-impervious material is present within the breathable zones of reduced stiffness 70, thus helping to prevent unwanted irritation. Furthermore, these breathable zones of reduced stiffness 70 are preferably formed so that only hydrophobic material is present, thus further reducing the possibility of moisture wicking to the leg regions, resulting in increased comfort and fit around the wearer's thighs.

Figure 3:
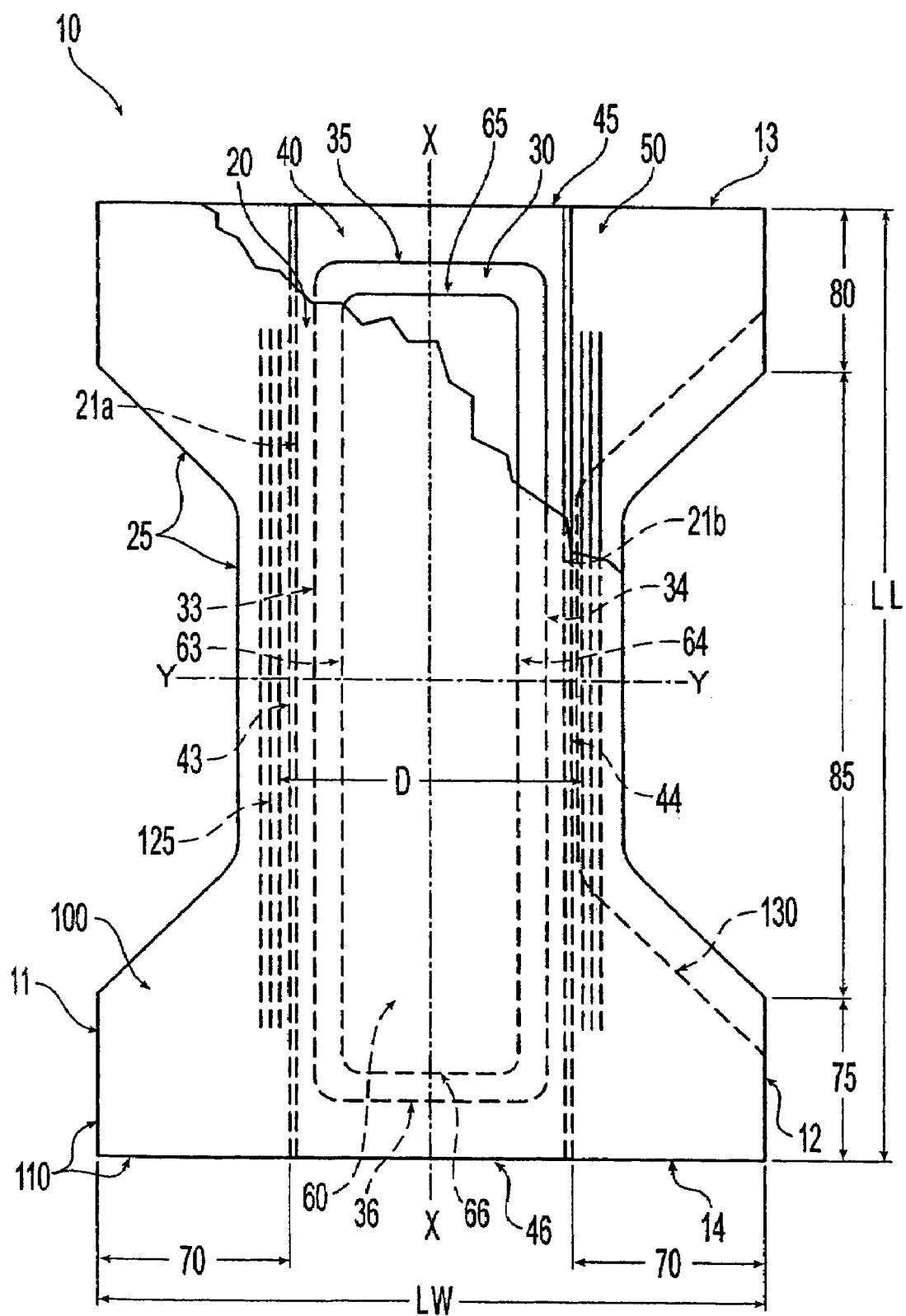
FIG. 3 is a partial cross-sectional view of a diaper embodiment of the absorbent article of the present invention with the surface of the diaper that contacts the wearer facing the viewer.

As shown in FIG. 3, the diaper 10 has a longitudinal axis X-X, a transverse, or lateral, axis Y-Y, a longitudinal length (LL), a lateral width (LW), longitudinal end edges 13, 14 and lateral side edges 11, 12. Although it is not necessary, the diaper 10 generally has a front waist region 75, a rear waist region 80 and an intermediate crotch region 85, i.e., a portion of the diaper adapted to engage the wearer's crotch to capture body exudates. Furthermore, the crotch region 85 has on either side a pair of leg openings 25 that give the diaper 10 a general hour-glass shape, with the leg openings 25 forming the lateral edges of the crotch region 85. Diaper ears 100 extend laterally outward at the front waist region 75 and the rear waist region 80. It should be noted, however, that the shape of the diaper is not critical and the diaper may take on any shape known in the art, including but not limited to rectangular.

The barrier cuffs 21a, 21b, and backsheet 50 preferably extends to the longitudinal end edges 13, 14 and to the lateral side edges 11, 12 of the diaper 10, so as to form the outer perimeter 110 of the diaper 10. Meanwhile, the topsheet 20 has a lateral width dimension smaller than that of the overall diaper perimeter 110. That is, the topsheet 20 does not extend to the lateral side edges 11, 12 of the diaper 10. Preferably, the topsheet 20 does not extend into the breathable zones of reduced stiffness 70. In this embodiment, the topsheet 20 should have a lateral width dimension larger than the lateral width dimension of the absorbent core 30, so that the topsheet 20 may be bonded to the barrier cuffs 21a, 21b at barrier cuff bonding points 22a, 22b, overlaying the barrier layer 40 and/or the backsheet 50, thus enclosing the absorbent core 30. Generally speaking, the topsheet 20 may have a lateral width substantially similar to the lateral width of the barrier layer 40, which will be described in more detail later, although this is not necessary.

Bonding of the topsheet 20 to the barrier cuffs 21a, 21b can be preformed by any conventional means known in the art, including but not limited to heat sealing, ultrasonic, adhesive bonding, etc. It is further contemplated that the bonding may be a continuous bonding strip or a series of discrete bonding points.

In a preferred embodiment, the barrier cuffs 21a, 21b include elastication with elastic strands 126. The elastic strands 126 may be manufactured by any means known in the art, and may be a single strand of elastic material or several strands of elastic material.

Alternatively, the backsheet 50 may have a dimension smaller than that of the overall diaper perimeter 110. That is, the backsheet 50 does not have to extend to the lateral side edges 11, 12 of the diaper 10. In this embodiment, the backsheet 50 should be larger in the lateral width dimension than the absorbent core 30, so that the backsheet 50 may be bonded to the barrier layer 40 and/or barrier cuffs 21a, 21b, so as to enclose the absorbent core 30.

Similarly, the barrier cuffs 21a, 21b may have a dimension smaller than that of the overall diaper perimeter 110. That is, the barrier cuffs 21a, 21b do not have to extend to the lateral side edges 11, 12 of the diaper 10. In this embodiment, the barrier cuffs 21a, 21b should be large enough to extend beyond the lateral edges of the topsheet 20, so that the barrier cuffs 21a, 21b may be bonded to the barrier layer 40 and/or backsheet 50, so as to enclose the absorbent core 30.

The absorbent core 30 has lateral edges 33, 34, longitudinal edges 35, 36, a longitudinal length, and a lateral width. Similarly, the barrier layer 40 has lateral edges 43, 44, longitudinal edges 45, 46, a longitudinal length, and a lateral width. The length and width dimensions of the barrier layer 40 are larger than the length and width dimensions of the absorbent core 30. That is, the lateral edges 43, 44 of the barrier layer 40 extend beyond the lateral edges 33, 34 of the absorbent core 30 and the longitudinal edges 45, 46 of the barrier layer 40 extend beyond the longitudinal edges 35, 36 of the absorbent core 30 so that the barrier layer 40 provides full leakage protection from all bodily exudates absorbed and contained by the absorbent core 30.

The optional acquisition layer 60 also has lateral edges 63, 64, longitudinal edges 65, 66, a longitudinal length, and lateral width. Preferably, the lateral width dimension of the absorbent core 30 should be larger than the lateral width dimension of the acquisition layer 60. That is, the lateral edges 33, 34 of the absorbent core 30 extend beyond the lateral edges 63, 64 of the acquisition layer 60. However, it should be noted that the lateral width dimension of the acquisition layer 60 is not critical and that the lateral edges 63, 64 of the acquisition layer 60 may extend up to and beyond the lateral edges 33, 34 of the absorbent core 30. Similarly, the length dimension of the acquisition layer 60 is not critical and may be smaller, equal to or larger than the length dimension of the absorbent core 30. Alternatively, the acquisition layer 60 may be omitted in its entirety.

The diaper 10 has leg gasketing regions 130, defined as the region of the diaper 10 circumferentially surrounding the leg openings 25. The diaper 10 preferably includes leg elastics 125 in at least a portion of the leg gasketing regions 130. The leg elastics 125 are provided to give the diaper 10 improved fit around the wearer's thighs thereby reducing lateral leakage and improving the diaper's appearance in use. As shown in FIG. 4, the leg elastics 125 may be bonded to either the barrier cuffs 21a, 21b, backsheet 50, or both. The leg elastics 125 may extend along a substantial portion of the leg gasketing regions 130, or they may extend only along portion of the leg gasketing regions 130. Alternatively, the leg elastics 125 may extend along the entire longitudinal length of the diaper 10. For example, as shown in FIG. 3, the leg elastics 125 may extend only along the portion of the leg gasketing regions 130 generally corresponding to the crotch region 85.

The leg elastics 125 may take on any configuration well known in the art. For example, the leg elastics 125 may each comprise a leg elastic member such as: a single strand of elastic material, several strands of elastic material, a rectangular elastic mesh, an elastic sheet, etc. If the leg elastics 125 comprise several strands of material, those strands may be parallel or non-parallel. The leg elastics 125 may be straight, and parallel with the longitudinal axis of the diaper 10, or they may be curved to follow the contour of the leg openings 25. Furthermore, the leg elastics 125 may be formed from a single elastic members in each leg gasketing region 130, or may be formed from a series of elastic members located circumferentially along each leg gasketing region 130. As seen in FIG. 3, the leg elastics 125 preferably comprise a pair of parallel elastic members separated in the lateral direction by a distance D, the leg elastic separation distance.

Preferably, the absorbent core 30 and the leg elastics 125 are arranged so that the lateral edges 33, 34 of the absorbent core 30 are disposed laterally inboard of the leg elastics 125. That is, the lateral edges 33, 34 of the absorbent core 30 are closer to the longitudinal centerline X-X than are the leg elastics 125. More preferably, the absorbent core 30 and the leg elastics 125 are arranged so that the lateral edges 33, 34 of the absorbent core 30 are disposed laterally inboard of the barrier cuff bonding points 22a, 22b while the leg elastics 125 are located outboard of the barrier cuff bonding points 22a, 22b.

Similarly, the barrier layer 40 and the leg elastics 125 are preferably arranged so that the lateral edges 43, 44 of the barrier layer 40 are disposed laterally inboard of the leg elastics 125; that is, the lateral edges 43, 44 of the barrier layer 40 are between the leg elastics 125 and the lateral edges 33, 34 of the absorbent core 30.

Figure 4:
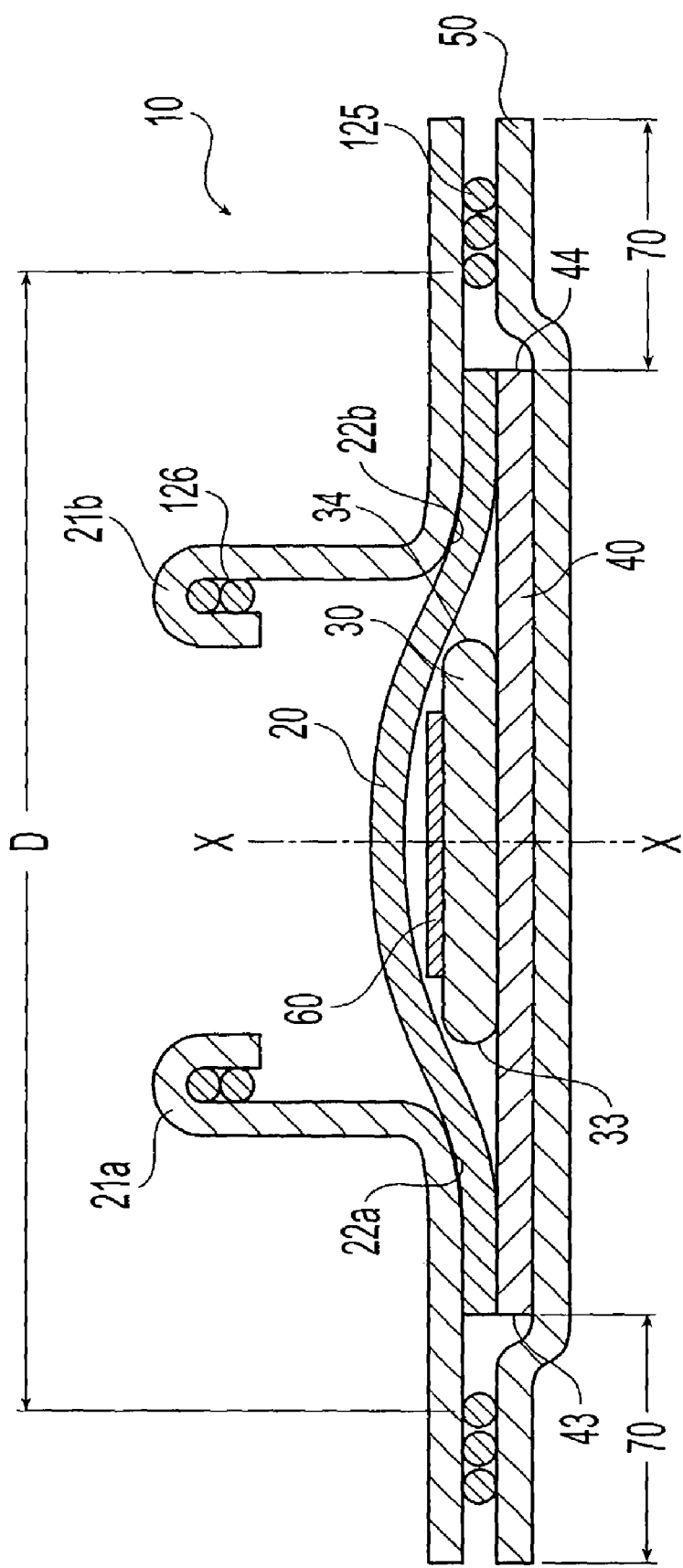
FIG. 4 is a cross sectional view of the absorbent article in FIG. 3.

Finally, the topsheet 20 and the leg elastics 125 are preferably arranged so that the lateral edges of the topsheet 20 are disposed laterally inboard of the leg elastics 125 and anchored to the barrier cuffs 21a, 21b by the barrier cuff bonding points 22a, 22b as shown in FIG. 4.

By reducing the size of the liquid-impervious barrier layer 40, particularly by reducing the lateral width dimension of the barrier layer 40 so that it does not extend laterally beyond the leg elastics 125, breathable zones of reduced stiffness 70 are advantageously created. As shown, these breathable zones of reduced stiffness 70 extend from the lateral edges 43, 44 of the barrier layer 40 to the diaper's outer perimeter 110 inclusive of the leg elastics 125, leg opening 25 and diaper ears 100. The breathable zones of reduced stiffness 70 are defined as areas of the diaper 10, which do not include any liquid-impervious material. Because the breathable zones of reduced stiffness 70 are devoid of any liquid-impervious material, they provide regions of the diaper which permit the escape of moist vapor from within the diaper 10. Thus, these breathable zones of reduced stiffness 70 reduce the moisture in the environment of the baby's skin surface, thereby reducing irritation and rashes associated with such moisture.

Furthermore, the absence of a barrier layer 40 within these breathable zones of reduced stiffness 70 also makes the diaper 10 less stiff around the leg openings 25. The reduction in stiffness is attributable to the reduction in the number of layers involved in the diaper 10 in these zones, and more specifically to the elimination of plastic film typically used to make barrier layers 40, which are known to be relatively stiff as compared to the materials typically used for topsheets 20, barrier cuffs 21a, 21b, and backsheets 50. Since there is no liquid-impervious material in the breathable zones of reduced stiffness 70, the present invention provides a softer web of material upon which the leg elastics 125 act upon to form the seal around the legs. This reduces problems of fit and proper sealing (leak prevention) associated with the prior art. Furthermore, as lower-force elastics may be used for the leg elastics 125 of the present invention, it also reduces problems of skin irritation associated with the higher-force elastics required with known diapers. Further still, the reduction of the amount of plastic film used as barrier material reduces the amount of noise generally associated with the movement of the diaper. This problem is particularly acute in the leg gather regions, which are subject to, considerable amount of motion.

Furthermore, by reducing the size of the liquid-impervious barrier layer 40 and creating the breathable zones of reduced stiffness 70 without requiring the barrier layer 40 to be wrapped around the absorbent core 30, the present invention eliminates the disadvantages of known absorbent articles in which body exudates land on top of the portions of the liquid-impervious strip overlaying the top of the absorbent core 30, thus resulting in the passage of body exudates to the outer layer of the diaper.

The inventors of the present invention have also discovered that providing a zone surrounding the wearer's thighs in which only hydrophobic liquid-pervious material is present, results in a better-fitting disposable diaper having increased breathability, softness and flexibility while still preventing leakage. That is, the present inventors have discovered that a better-fitting, less irritating disposable diaper can be produced by providing a zone comprising a laminate of only hydrophobic material, as compared to prior art diapers which involve a laminate of a hydrophobic backsheet, a fluid impervious film, and a hydrophilic topsheet.

This inventive design is provided by using a hydrophilic topsheet that does not extend to the outer perimeter of a diaper. More specifically, the inventive article is provided by using a hydrophilic topsheet that does not extend into the breathable zones of reduced stiffness 70, as described above.

Turning now to a description of the materials used for the various components, the barrier layer 40 may be manufactured from any liquid-impervious material known in the art to prevent leakage of liquid discharges absorbed by the absorbent core 30. More preferably, the barrier layer 40 is manufactured from a polyethylene, polypropylene, polyester, or similar polymeric film.

The topsheet 20 may be manufactured from any liquid-pervious material known in the art that permits passage of liquid therethrough. Preferably, the topsheet 20 is manufactured from a hydrophilic non-woven material, more preferably the topsheet 20 is manufactured from a zone coated hydrophilic non-woven material, as such materials readily allows the passage of liquids to the underlying absorbent core 30.

The backsheet 50 may be manufactured from any appropriate material known in the art capable of providing the necessary structural support for the diaper 10 as well as the desired aesthetic appearance for the outside of the diaper 10. Preferably, the backsheet 50 is manufactured from a liquid and gas-pervious material, such as a hydrophobic non-woven material.

The absorbent core 30 may be manufactured from any appropriate material known in the art capable of absorbing and retaining liquids and other body exudates in the amounts (and flow rates) typically produced by the human body. The absorbent core 30 may be manufactured from any liquid-absorbing material commonly used in disposable diapers, including but not limited to comminuted wood pulp, tissue including tissue wraps and tissue laminates, absorbent foams, absorbent sponges, superabsorbent polymers, absorbent gelling materials, meltblown polymers including coform, creped cellulose wading, chemically stiffened, modified or cross-linked cellulosic fibers, or any equivalent material or combination of materials.

The barrier cuffs 21a, 21b may be manufactured from any material known in the art capable of forming a barrier to laterally flowing urine and/or pockets into which solid fecal material is collected and contained. Furthermore, the barrier cuffs 21a, 21b should be able to slow and/or prevent the passage of the fluidic fecal material, thus permitting it to be absorbed by the underlying absorbent core 30. Preferably, the barrier cuffs 21a, 21b are manufactured from a hydrophobic liquid-pervious material and are attached to the topsheet at barrier cuff bonding points 22a, 22b.

The optional acquisition layer 60 may be manufactured from any material known in the art capable of distributing and spreading liquid body exudate to the absorbent core 30. Preferably, the acquisition layer 60 may be manufactured from a tissue, airlaid fluff pulp, or synthetic nonwoven material.

The present invention has been described in connection with the preferred embodiments. These embodiments, however, are merely for example and the invention is not restricted thereto. It will be understood by those skilled in the art that other variations and modifications can easily be made while remaining within the scope of the invention as defined by the appended claims.

What is claimed:

1. An absorbent article having a longitudinal axis, a lateral axis, a longitudinal length, a lateral width, longitudinal end edges and lateral side edges, a front waist region, a rear waist region, an intermediate crotch region interconnecting the front and rear waist regions, and a pair of leg openings on the lateral sides of the crotch region, the article further comprising:
   a liquid-pervious backsheet;
   a liquid-pervious topsheet;
   a pair of liquid-pervious barrier cuffs bonded to the topsheet;
   an absorbent core disposed between the topsheet and the backsheet;
   a liquid-impervious barrier layer disposed between the absorbent core and the backsheet; and
   leg elastic members located in at least a portion of the crotch region adjacent to the leg openings;
   wherein the barrier layer is not present in the portion of the article where the leg elastic members are located, the barrier layer does not wrap around the core, and the barrier cuffs and the backsheet extend past lateral edges of the barrier layer and terminate at the lateral side edges of the absorbent article.

2. The absorbent article of claim 1, wherein the topsheet is not present in the portion of the article where the leg elastic members are located.

3. The absorbent article of claim 1, wherein the barrier cuffs and the backsheet are formed of a hydrophobic material.

4. The absorbent article of claim 1, wherein the absorbent core has lateral edges which are located laterally inboard of the leg elastics.

5. The absorbent article of claim 4, further comprising bonding points where the barrier cuffs are bonded to the topsheet, wherein the lateral edges of the absorbent core are located laterally inboard of the bonding points.

6. The absorbent article of claim 4, wherein the absorbent core has a longitudinal length which is less than a longitudinal length of the absorbent article, and has longitudinal edges which do not extend to the absorbent article's longitudinal end edges.

7. The absorbent article of claim 1, wherein the barrier layer has lateral edges which are located laterally inboard of the leg elastics.

8. The absorbent article of claim 7, wherein the barrier layer has a longitudinal length that extends to the absorbent article's longitudinal end edges.

9. The absorbent article of claim 1, wherein the topsheet has lateral edges which are located laterally inboard of the leg elastics.

10. The absorbent article of claim 1, wherein the core, the barrier layer, and the topsheet all have lateral edges which are located laterally inboard of the leg elastics.

11. The absorbent article of claim 1, wherein the portion of the crotch region where the leg elastics are located and where the barrier layer does not extend form breathable regions of reduced stiffness.

12. The absorbent article of claim 1, wherein the leg elastics comprise a pair of generally straight elastic members, each generally parallel to a longitudinal axis of the article, the elastic members being laterally separated from each other by a leg elastic separation distance.

13. The absorbent article of claim 12, wherein the absorbent core:
   is generally rectangular;
   has a lateral width which is less than the leg elastic separation distance; and
   has lateral edges which are located laterally inboard of the elastic members.

14. The absorbent article of claim 13, wherein the absorbent core has a longitudinal length which is less than the longitudinal length of the absorbent article, and has longitudinal edges which do not extend to the absorbent article's longitudinal end edges.

15. The absorbent article of claim 12, wherein the barrier layer:
   is generally rectangular;
   has a lateral width which is less than the leg elastic separation distance; and
   has lateral edges which are located laterally inboard of the elastic members.

16. The absorbent article of claim 15, wherein the barrier layer has a longitudinal length that extends to the absorbent article's longitudinal end edges.

17. An absorbent article having a longitudinal axis, a lateral axis, a longitudinal length, a lateral width, longitudinal end edges and lateral side edges, a front waist region, a rear waist region, an intermediate crotch region interconnecting the front and rear waist regions, and a pair of leg openings on the lateral sides of the crotch region, the article further comprising:
   a liquid-pervious hydrophobic backsheet;
   a liquid-pervious hydrophilic topsheet;
   a pair of liquid-pervious hydrophobic barrier cuffs bonded to the topsheet;
   an absorbent core disposed between the topsheet and the backsheet;
   a liquid-impervious barrier layer disposed between the absorbent core and the backsheet; and
   leg elastic members located in at least a portion of the crotch region adjacent to the leg openings;
   wherein the barrier layer is not present in the portion of the article where the leg elastic members are located, and the barrier cuffs and the backsheet extend past lateral edges of the barrier layer and terminate at the lateral side edges of the absorbent article.

18. The absorbent article of claim 17, wherein the topsheet is not present in the portion of the article where the leg elastic members are located.

19. The absorbent article of claim 17, wherein the absorbent core has lateral edges which are located laterally inboard of the leg elastics.

20. The absorbent article of claim 19, further comprising bonding points where the barrier cuffs are bonded to the topsheet, wherein the lateral edges of the absorbent core are located laterally inboard of the bonding points.

21. The absorbent article of claim 19, wherein the absorbent core has a longitudinal length which is less than the longitudinal length of the absorbent article, and has longitudinal edges which do not extend to the absorbent article's longitudinal end edges.

22. The absorbent article of claim 17, wherein the barrier layer has lateral edges which are located laterally inboard of the leg elastics.

23. The absorbent article of claim 22, wherein the barrier layer has a longitudinal length that extends to the absorbent article's longitudinal end edges.

24. The absorbent article of claim 17, wherein the topsheet has lateral edges which are located laterally inboard of the leg elastics.

25. The absorbent article of claim 17, wherein the core, the barrier layer, and the topsheet all have lateral edges which are located laterally inboard of the leg elastics.

26. The absorbent article of claim 17, wherein the portion of the crotch region where the leg elastics are located and where the barrier layer does not extend form breathable regions of reduced stiffness.

27. The absorbent article of claim 17, wherein the leg elastics comprise a pair of generally straight elastic members, each generally parallel to the longitudinal axis of the article, the elastic members being laterally separated from each other by a leg elastic separation distance.

28. The absorbent article of claim 27, wherein the absorbent core:
    is generally rectangular;
    has a lateral width which is less than the leg elastic separation distance; and
    has lateral edges which are located laterally inboard of the elastic members.

29. The absorbent article of claim 28, wherein the absorbent core has a longitudinal length which is less than the longitudinal length of the absorbent article, and has longitudinal edges which do not extend to the absorbent article's longitudinal end edges.

30. The absorbent article of claim 27, wherein the barrier layer:
    is generally rectangular;
    has a lateral width which is less than the leg elastic separation distance; and
    has lateral edges which are located laterally inboard of the elastic members.

31. The absorbent article of claim 30, wherein the barrier layer has a longitudinal length that extends to the absorbent article's longitudinal end edges.

32. An absorbent article having a longitudinal axis, a lateral axis, a longitudinal length, a lateral width, longitudinal end edges and lateral side edges, a front waist region, a rear waist region, and an intermediate crotch region interconnecting the front and rear waist regions, the article further comprising:
    a liquid-pervious hydrophobic backsheet;
    a liquid-pervious hydrophilic topsheet;
    a pair of liquid-pervious hydrophobic barrier cuffs bonded to the topsheet;
    an absorbent core disposed between the topsheet and the backsheet;
    a liquid-impervious barrier layer disposed between the absorbent core and the backsheet, the barrier layer having longitudinal edges and lateral edges; and
    breathable zones of reduced stiffness located in the portions of the article beyond the lateral edges of the barrier layer,
    wherein the barrier cuffs and the backsheet extend past the lateral edges of the barrier layer and terminate at the lateral side edges of the absorbent article.

33. The article of claim 32, wherein the breathable zones of reduced stiffness comprise portions of the absorbent article which do not encompass any liquid-impervious material.

34. The article of claim 32, wherein the breathable zones of reduced stiffness comprise portions of the absorbent article which do not encompass any hydrophilic material.

35. The article of claim 32, wherein the breathable zones of reduced stiffness comprise portions of the absorbent article which do not encompass any liquid-impervious or hydrophilic material.

36. The absorbent article of claim 32, further comprising leg elastic members located in at least a portion of the crotch region.

37. The absorbent article of claim 36, wherein the absorbent core has lateral edges which are located laterally inboard of the leg elastics.

38. The absorbent article of claim 37, further comprising bonding points where the barrier cuffs are bonded to the topsheet, wherein the lateral edges of the absorbent core are located laterally inboard of the bonding points.

39. The absorbent article of claim 37, wherein the absorbent core has a longitudinal length which is less than the longitudinal length of the absorbent article, and has longitudinal edges which do not extend to the absorbent article's longitudinal end edges.

40. The absorbent article of claim 36, wherein the barrier layer lateral edges are located laterally inboard of the leg elastics.

41. The absorbent article of claim 40, wherein the barrier layer has a longitudinal length that extends to the absorbent article's longitudinal end edges.

42. The absorbent article of claim 36, wherein the topsheet has lateral edges which are located laterally inboard of the leg elastics.

43. The absorbent article of claim 36, wherein the core, the barrier layer, and the topsheet all have lateral edges which are located laterally inboard of the leg elastics.

44. The absorbent article of claim 36, wherein the leg elastics comprise a pair of generally straight elastic members, each generally parallel to the longitudinal axis of the article, the elastic members being laterally separated from each other by a leg elastic separation distance.

45. The absorbent article of claim 44, wherein the absorbent core:
    is generally rectangular;
    has a lateral width which is less than the leg elastic separation distance; and
    has lateral edges which are located laterally inboard of the elastic members.

46. The absorbent article of claim 45, wherein the absorbent core has a longitudinal length which is less than the longitudinal length of the absorbent article, and has longitudinal edges which do not extend to the absorbent article's longitudinal end edges.

47. The absorbent article of claim 44, wherein the barrier layer:
    is generally rectangular;
    has a lateral width which is less than the leg elastic separation distance; and
    has lateral edges which are located laterally inboard of the elastic members.

48. The absorbent article of claim 47, wherein the barrier layer has a longitudinal length that extends to the absorbent article's longitudinal end edges.

* * * * *